(12) United States Patent
Mochizuki

(10) Patent No.: US 6,875,177 B2
(45) Date of Patent: Apr. 5, 2005

(54) ULTRASONIC DIAGNOSTIC APPARATUS

(75) Inventor: Takashi Mochizuki, Mitaka (JP)

(73) Assignee: Aloka Co., Ltd., Tokyo (JP)

( * ) Notice: Subject to any disclaimer, the term of this patent is extended or adjusted under 35 U.S.C. 154(b) by 210 days.

(21) Appl. No.: 10/181,140

(22) PCT Filed: Nov. 15, 2001

(86) PCT No.: PCT/JP01/09987

§ 371 (c)(1), (2), (4) Date: Jul. 9, 2002

(87) PCT Pub. No.: WO02/39901

PCT Pub. Date: May 23, 2002

(65) Prior Publication Data

US 2003/0032882 A1 Feb. 13, 2003

(30) Foreign Application Priority Data

Nov. 15, 2000 (JP) ........................................ 2000-348357

(51) Int. Cl.$^7$ ................................................ A61B 8/00
(52) U.S. Cl. ...................................... 600/447; 128/916
(58) Field of Search ............................ 600/437, 440–441, 600/443, 447, 454–456, 458; 73/625–626; 128/916; 367/7, 11, 103

(56) References Cited

U.S. PATENT DOCUMENTS

| | | | | |
|---|---|---|---|---|
| 4,766,905 A | * | 8/1988 | Namekawa | 600/454 |
| 4,993,417 A | * | 2/1991 | Seo | 600/455 |
| 5,081,996 A | * | 1/1992 | Kawasaki et al. | 600/455 |
| 5,144,954 A | * | 9/1992 | Satake | 600/455 |
| 5,233,993 A | | 8/1993 | Kawano | 128/660.07 |
| 5,239,413 A | | 8/1993 | Kawano | 128/660.07 |
| 5,415,171 A | * | 5/1995 | Goh et al. | 600/443 |
| 5,690,113 A | * | 11/1997 | Sliwa et al. | 600/443 |
| 5,720,291 A | * | 2/1998 | Schwartz | 600/456 |
| 5,776,063 A | * | 7/1998 | Dittrich et al. | 600/408 |
| 5,840,034 A | * | 11/1998 | Amemiya et al. | 600/444 |
| 5,961,463 A | | 10/1999 | Rhyne et al. | 600/458 |
| 5,993,390 A | * | 11/1999 | Savord et al. | 600/437 |
| 6,095,980 A | * | 8/2000 | Burns et al. | 600/453 |
| 6,139,500 A | * | 10/2000 | Clark | 600/443 |
| 6,245,017 B1 | * | 6/2001 | Hashimoto et al. | 600/447 |
| 6,544,175 B1 | * | 4/2003 | Newman | 600/437 |
| 6,673,019 B2 | * | 1/2004 | Kamiyama | 600/443 |
| 6,716,174 B1 | * | 4/2004 | Li | 600/447 |

FOREIGN PATENT DOCUMENTS

| | | |
|---|---|---|
| JP | 4-183457 | 6/1992 |
| JP | 5-344975 | 12/1993 |
| JP | 0 952 461 | 10/1999 |
| JP | 11-299786 | 11/1999 |
| JP | 2000-60855 | 2/2000 |

* cited by examiner

Primary Examiner—Francis J. Jaworski
(74) Attorney, Agent, or Firm—Koda & Androlia (57) ABSTRACT

An ultrasonic diagnostic apparatus forms a three-dimensional echo data acquisition space. A beam address array is composed of a plurality of ultrasonic beam addresses constituting a three-dimensional echo data acquisition space. The beam address array is divided into a plurality of address groups, and address scanning is repeated twice for each of the address groups. Thus, when a differential operation or the like of two data items obtained at the same beam position is performed, the time interval between acquisition of the two data pieces becomes short. The existence or behavior of an ultrasonic contrast agent within tissue of a living body is displayed as a three-dimensional differential image.

18 Claims, 6 Drawing Sheets

ULTRASONIC DIAGNOSTIC APPARATUS

TECHNICAL FIELD

The present invention relates to an ultrasonic diagnostic apparatus, and more specifically to an ultrasonic diagnostic apparatus for forming a three-dimensional (3D) echo data acquisition space.

BACKGROUND ART

Ultrasonic diagnostic apparatuses for forming a three-dimensional ultrasonic image have been put into practice. Such an ultrasonic diagnostic apparatus comprises an array transducer unit having a plurality of transducer elements for effecting electronic scanning with an ultrasonic beam, a mechanical scanning mechanism for moving the array transducer unit for mechanical scanning, and so on. With the above-described structure, an ultrasonic diagnostic apparatus creates a three-dimensional echo data acquisition space which is composed of a plurality of scanning planes, thus forming a three-dimensional ultrasonic image (for example, a projection image) based on a large number of echo data acquired within the three-dimensional echo data acquisition space. The scanning plane is formed by electronic scanning of the ultrasonic beams. Namely, the scanning plane is composed of a plurality of ultrasonic beams (sound rays). Accordingly, the three-dimensional echo data acquisition space is a collection of ultrasonic beams (an ultrasonic beam array). On the other hand, other types of ultrasonic diagnostic apparatuses which form a three-dimensional echo data acquisition space using a two-dimensional (2D) array transducer which includes a plurality of transducer elements arranged two-dimensionally have also been proposed. These apparatuses create a three-dimensional echo data acquisition space by two-dimensional electronic scanning of ultrasonic beams (without moving the transducers for mechanical scanning).

In recent years, ultrasonic diagnostic apparatuses for forming an image by using echoes reflected from an ultrasonic contrast agent which has been injected into a tissue (for example, a blood vessel) of a living body have also been put to use. Normally, echoes from blood are weaker than echoes from tissue, whereas echoes from an ultrasonic contrast agent are relatively strong. These apparatuses make use of this characteristic to form an image of a blood vessel. Specifically, an ultrasonic contrast agent is composed of a very large number of microbubbles (very small bubbles having a predetermined structure). When the ultrasonic wave reaches the microbubbles, the microbubbles destruct or disappear. At the same time, reflected waves which are distorted (echoes) are generated. Using the basic wave components or higher harmonic wave components of these echoes, an ultrasonic image is formed.

It is possible to clearly visualize the existence or behavior of an ultrasonic contrast agent by comparing two items of echo data which are acquired before and after destruction or disappearance of the microbubbles forming the ultrasonic contrast agent, or by comparing two items of echo data which are acquired before and after movement of the ultrasonic contrast agent.

In general, an ultrasonic contrast agent is continuously injected into tissue of a living body for a determined period once the injection has started. When two items of data (echo data or pixel data) which are acquired at the same beam address are compared, it is difficult to accurately form an image of the ultrasonic contrast agent if a time interval between the acquisition of these two items of data is too long. For example, assume that at a certain local region within a blood vessel, the microbubbles of the ultrasonic contrast agent destruct or disappear at the first irradiation of ultrasonic waves, and the second irradiation of the ultrasonic waves is not performed immediately after the first irradiation. Namely, assume that the second ultrasonic irradiation is not performed until a sufficient amount of the ultrasonic contrast agent is supplied to that local region through the blood flow. In such a case, there is not a significant difference between the data obtained from the first irradiation and data obtained from the second irradiation.

Further explanation will be given. Conventionally, when the three-dimensional echo data acquisition space is formed, the scanning plane is scanned (mechanically, for example) at a fixed rate, as described above. In such scanning, one scanning operation of the scanning plane requires, for example, one second. Accordingly, when the scanning operation of the scanning plane is carried out twice successively, the time interval between the two items of data acquired at the same beam address by these two scanning operations, results in, for example, one second. This makes it difficult to detect an instantaneous phenomenon by comparing the two items of data.

DISCLOSURE OF THE INVENTION

The present invention was conceived in view of the aforementioned drawbacks of the related art and an object of the present invention is to provide a new ultrasonic beam scanning method for forming a three-dimensional echo data acquisition area.

Another object of the present invention is to provide optimum beam scanning for displaying, as an ultrasonic image, behavior or change of an ultrasonic contrast agent.

Still another object of the present invention is to enable measurement of an instantaneous phenomenon within a three-dimensional data acquisition area.

(1) In order to achieve the foregoing objects, in accordance with one aspect of the present invention, an ultrasonic diagnostic apparatus comprises group setting means for setting a plurality of address groups with regard to a beam address array; sequence setting means for setting an iterative sequence of beam addresses, which is used for selecting a plurality of beam addresses constituting the beam address array while selecting beam addresses repeatedly for each of the address groups; address selecting means for selecting the beam addresses in accordance with the iterative sequence which is set by the sequence setting means; beam forming means for forming an ultrasonic beam at a beam address selected by means of the address selecting means; and image forming means for forming an ultrasonic image based on echo data acquired by formation of the ultrasonic beam.

According to the above structure, in the process of selecting a series of addresses with regard to the beam address array, beam addresses are repeatedly selected for each address group. This makes it possible to shorten the time interval between a plurality of echo data acquired at the same beam address compared to a conventional scanning method. It is also possible to change the time interval as desired, by changing a method of setting the address groups.

Preferably, a three-dimensional echo data acquisition space is formed by forming the ultrasonic beam at each of the plurality of beam addresses constituting the beam address array, and the ultrasonic image is an image representing the three-dimensional echo data acquisition space.

Preferably, the three-dimensional echo data acquisition space is divided into a plurality of partial spaces, and each of the address groups corresponds to each of the partial spaces.

Preferably, each of the partial spaces is composed of one or more scanning planes, and each of the scanning planes is composed of a plurality of ultrasonic beams which are sequentially formed in the electronic scanning direction.

Preferably, the image forming means uses two items of echo data obtained at a same beam address at a predetermined time interval, to form an ultrasonic image representing a change within the predetermine time interval.

Preferably, the image forming means includes a differential operation unit for executing a differential operation with regard to the two items of echo data.

Preferably, the ultrasonic image is an image representing an ultrasonic contrast agent injected into a living body.

Preferably, the beam forming means includes a transducer unit having a one-dimensional array transducer for electronically scanning the ultrasonic beams; and a mechanical scanning mechanism for moving the transducer unit for mechanical scanning.

Preferably, the mechanical scanning mechanism moves the transducer unit for mechanical scanning in accordance with the iterative sequence.

Preferably, in the process of moving the transducer unit forward in the mechanical scanning direction, the mechanical scanning mechanism causes the transducer unit to move backward in steps.

Preferably, the beam forming means includes a two-dimensional array transducer, and the ultrasonic beams are electronically scanned two-dimensionally.

Preferably, the beam forming means performs scanning of the ultrasonic beams in the first scanning direction to form a scanning plane, and moves the position of the scanning plane forward in the second scanning direction, and in the process of moving the position of the scanning plane forward in the second scanning direction, such forward movement is repeated for each section corresponding to each of the address groups.

Preferably, the plurality of address groups are provided in a matrix with regard to the beam address array.

Preferably, each of the address groups is composed of a plurality of beam address lines, and ultrasonic beams are electronically scanned for each of the beam address lines.

Preferably, each of the address groups is composed of a plurality of beam addresses randomly provided in the beam address array.

Preferably, the beam address array is composed of a plurality of receiving beam addresses, and at each of the address groups, for one transmission and reception of the ultrasonic beam, one transmitting beam is formed and a plurality of receiving beams are concurrently formed.

(2) In order to achieve the foregoing objects, in accordance with another aspect of the present invention, an ultrasonic diagnostic apparatus comprises a setting section for setting a plurality of address groups with regard to a two-dimensional beam address array; a sequencer for setting a sequence used for selecting a plurality of beam addresses constituting the beam address array while selecting beam addresses repeatedly for each of the address groups; an address controller for selecting beam addresses in accordance with the sequence set by the sequencer; a beam former for forming an ultrasonic beam at a beam address selected by the address controller; and an image forming section for forming an ultrasonic image based on echo data obtained by formation of the ultrasonic beam.

Preferably, for each of the address groups, a step of sequentially selecting a plurality of beam addresses of the address group is repeated at least twice.

Preferably, the beam address array is composed of a plurality of receiving beam addresses, and for each of the address groups, a step of collectively selecting a plurality of receiving beam addresses of the address group is repeated at least twice.

(3) In accordance with still another aspect of the present invention, an ultrasonic diagnostic apparatus for forming a three-dimensional echo data acquisition space within tissue of a living body in which an ultrasonic contrast agent is injected, comprises means for setting a plurality of partial spaces in the three-dimensional echo data acquisition space; means for effecting beam scanning with regard to the three dimensional echo data acquisition space by repeating transmission and reception of an ultrasonic wave a plurality of times for each of the partial spaces; means for forming a partial image representing the existence or behavior of the ultrasonic contrast agent based on echo data obtained by transmitting and receiving an ultrasonic wave a plurality of times for each of the partial spaces; and means for synthesizing partial images regarding the plurality of partial spaces to form an ultrasonic image.

(4) In accordance with an even further aspect of the present invention, a two-dimensional ultrasonic beam scanning method for forming a three-dimensional echo data acquisition space, comprises the steps of determining a plurality of partial spaces with regard to the three dimensional echo data acquisition space; setting a sequence used for sequentially selecting the plurality of partial spaces while selecting each of the plurality of partial spaces a plurality of times; and two-dimensionally scanning an ultrasonic beam in accordance with the sequence.

BRIEF DESCRIPTION OF THE DRAWINGS

These and other objects of the invention will be explained in the description below, in connection with the accompanying drawings, in which.

DESCRIPTION OF THE PREFERRED EMBODIMENTS

Preferred embodiments of the present invention will be described with reference to the drawings.

Figure 1:
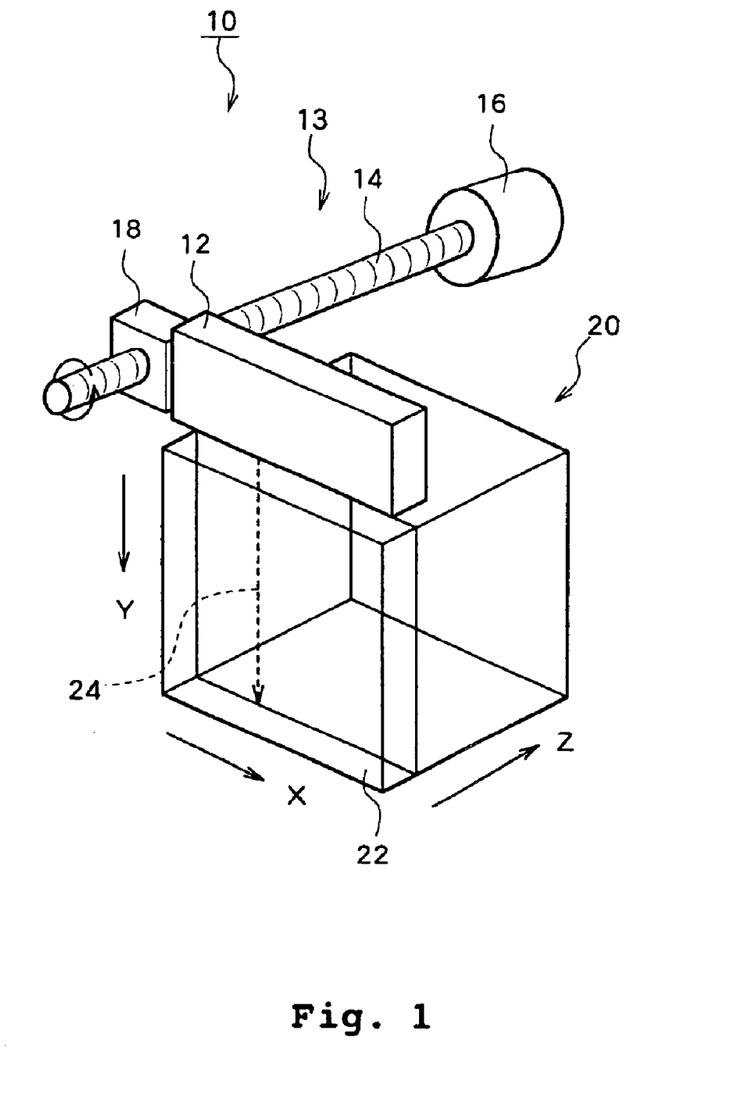
FIG. 1 is a conceptual view showing a main part of an ultrasonic probe for use in acquisition of three-dimensional echo data according to an embodiment of the present invention.

FIG. 1 is a perspective view schematically showing a structure of an ultrasonic probe 10 used for acquiring three-dimensional echo data, which is contained in an ultrasonic diagnostic apparatus.

A three-dimensional echo data acquiring ultrasonic probe 10 includes an array transducer unit 12, a mechanical scanning mechanism 13, and a position detector (not shown). The array transducer unit 12 includes an array transducer (not shown) which is composed of a plurality of transducer elements arranged in a line. This array transducer unit 12 is used for electronic scanning of an ultrasonic beam 24. While an example of electronic linear scanning is illustrated in FIG. 1, electronic scanning includes other types of scanning such as electronic sector scanning. By the electronic scanning of the ultrasonic beam 24, a scanning plane 22, which is of a rectangular shape in FIG. 1, is formed. With electronic sector scanning, on the other hand, the scanning plane 22 would have a sector shape. Normally, one transmission/reception of an ultrasonic wave produces one transmitting beam and one receiving beam. However, it is possible to form a plurality of receiving beams simultaneously with respect to one transmitting beam (a broad transmitting beam), as will be described later.

The mechanical scanning mechanism 13 includes a driving motor 16, a feed screw 16, and a bearing part 18 for moving the array transducer unit 12 for mechanical scanning. Specifically, because the bearing part 18 is fitted onto the feed screw 14, when the driving motor 16 is rotated in one direction, the array transducer unit 12 moves toward one direction (forward direction) in the Z direction. When the driving motor 16 is rotated in the other direction, on the other hand, the array transducer unit 12 moves to the other direction (backward direction) in the Z direction. As will be described later, during the forward movement of the array transducer unit 12 in the Z direction, the array transducer unit 12 is caused to move backward at respective steps of the forward movement. Namely, the mechanical scanning is carried out in a manner similar to a backstitch movement.

A wave transmitting/receiving surface (a bottom surface in FIG. 1) of the array transducer unit 12 may be brought into direct contact with a surface of a living body. Alternatively, a coupling liquid may be provided between the wave transmitting/receiving surface and the surface of the living body. In the latter case, the coupling liquid is stored within a case (not shown) of the ultrasonic probe 12. As will be described in further detail later, when a two-dimensional array transducer is used, the above-described mechanical scanning can be replaced by electronic scanning. Namely, electronic scanning of the ultrasonic beams can be effected in both X and Z directions. While the ultrasonic probe 10 is preferably used in contact with the surface of a living body, it is also possible to insert the ultrasonic probe 10 into a tubular tissue such as esophagus, rectum, blood vessel, and so on. Further, whereas a subject of diagnosis is preferably a human body, it can also be an animal other than a human.

As described above, the electronic scanning (the first scanning) of the ultrasonic beam 24 and the mechanical scanning (the second scanning) of the scanning plane 22 are performed. In general, electronic scanning is performed at a much higher rate than mechanical scanning. Therefore, by carrying out mechanical scanning while electronic scanning is being repeated, a three-dimensional echo data acquisition space 20 is formed. The three-dimensional echo data acquisition space 20 can be regarded as a collection of many scanning planes 22. While the three-dimensional echo data acquisition space 20 in FIG. 1 is cubic, when electronic sector scanning is effected, it would be substantially a pyramid shape. In FIG. 1, the Y direction indicates a depth direction along the ultrasonic beam 24, the X direction indicates an electronic scanning direction (the first scanning direction), and the Z direction is a mechanical scanning direction (the second scanning direction).

Figure 2:
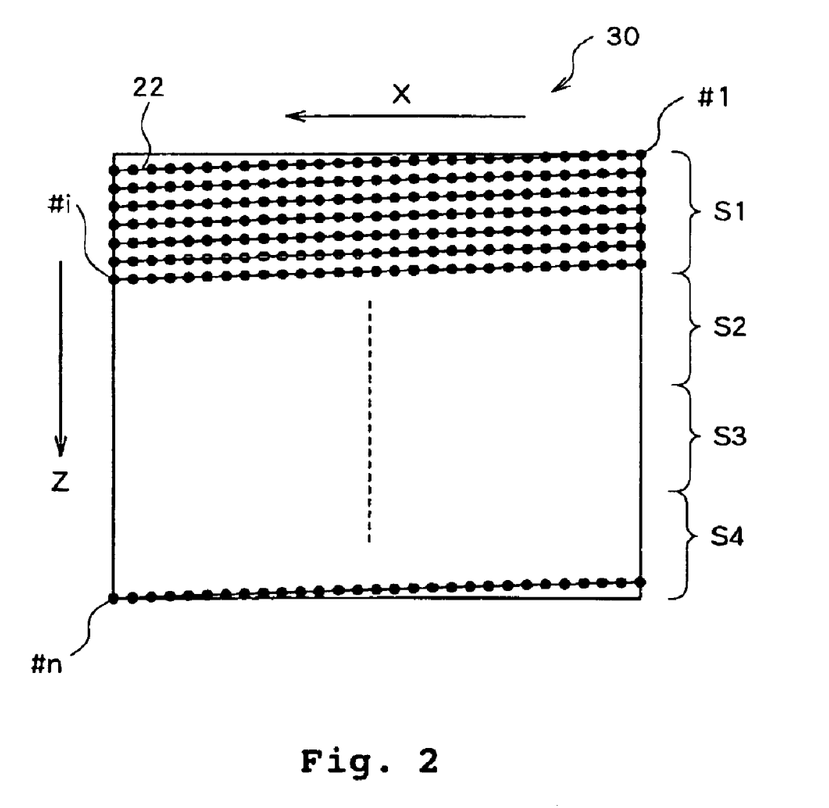
FIG. 2 is a diagram showing n beam addresses (a beam address array)

FIG. 2 shows a two-dimensional beam address array 30, which is formed on the X-Z plane. In FIG. 2, each beam address (a center point for forming an ultrasonic beam) is indicated by a block circle. More specifically, the beam address array 30 is composed of n beam addresses #1~#n. Formation of the ultrasonic beams (a transmitting wave beam and a receiving wave beam) at the respective beam addresses constituting the beam address array 30 results in formation of a three-dimensional echo data acquisition space. A plurality of beam addresses arranged in a line in the X direction (a beam address line) corresponds to a scanning plane 22. The scanning plane 22 is slightly inclined toward the Z direction (see FIG. 2), because, during the electronic scanning of the ultrasonic beams, mechanical scanning is also carried out by moving the scanning plane 22 in the direction normal to the electronic scanning direction. However, such an inclination of the scanning plane 22 can be in fact disregarded, as the rate of electronic scanning is typically higher than that of mechanical scanning. It is also possible to temporarily stop the array transducer unit 12 intermittently at the respective positions along the Z direction and carry out electronic scanning at the respective stop positions. (In this case, the scanning plane 22 is not inclined). Further, when a two-dimensional array transducer is employed, the above-mentioned inclination can be eliminated.

In the present embodiment, the n beam addresses (the beam address array 30) are virtually sectioned into a plurality of address groups, which are indicated by S1, S2, S3 and S4 in FIG. 2. For example, the address group S1 is composed of i beam addresses from the beam address #1 to the beam address #i. Similarly, each of other address groups S2 to S4 also contains i beam addresses. While it is preferable that all the address groups include the same number of beam addresses, the number of addresses may differ among the address groups. Also, the number of address groups (or the number of beam addresses forming each address group) may be variable and may be set by a user. Alternatively, these numbers may be variable and may be automatically set in accordance with the operation mode or the measuring condition.

In this embodiment, in the process of forming a single three-dimensional echo data acquisition space, for each address group, scanning of a series of beam addresses of that address group is carried out twice. Specifically, when attention is focused on the address group S1, for example, the beam addresses #1 to #i are first sequentially selected one by one (ultrasonic beams are sequentially formed), and then the beam addresses #1 to #i are sequentially selected one by one (ultrasonic beams are sequentially formed) once again. This iterative scanning is carried out for each of the address groups, so that finally the ultrasonic beams are formed twice for each of the beam addresses. Thus, a series of beam addresses are sequentially selected according to this "iterative sequence", thereby forming the three-dimensional echo data acquisition space. In this case, the array transducer unit 12 moves backward by a predetermined distance at the respective steps during the forward movement thereof in the Z direction. Then, the three-dimensional echo data acquisition spaces 20 are formed in a repeated manner as necessary. The three-dimensional echo data acquisition space 20 may be formed only when the forward scanning in the Z direction is carried out or may be formed during both the forward and backward scanning in the Z direction. In any case, when the three-dimensional echo data acquisition spaces 20 are formed repeatedly, the same iterative sequence may be applied or different iterative sequences may be applied. Further, while the number of scanning operations carried out for each address group is preferably twice, it can be set to three times or more.

Figure 3:
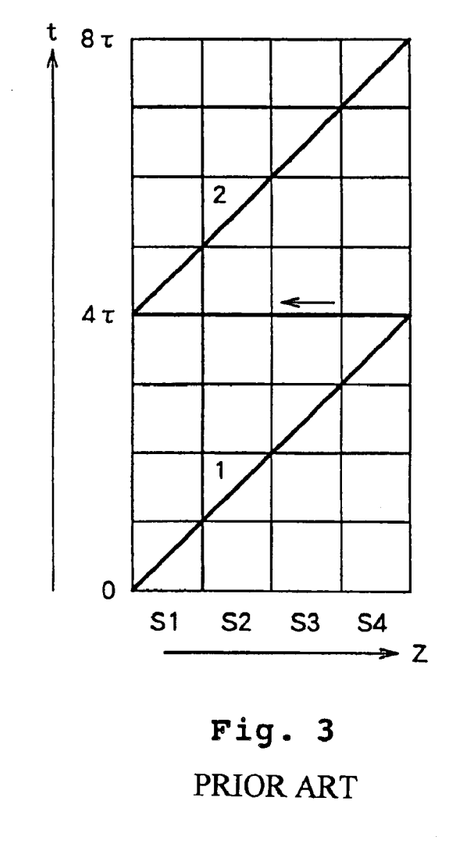
FIG. 3 a diagram for explaining a conventional address selection sequence.
Figure 4:
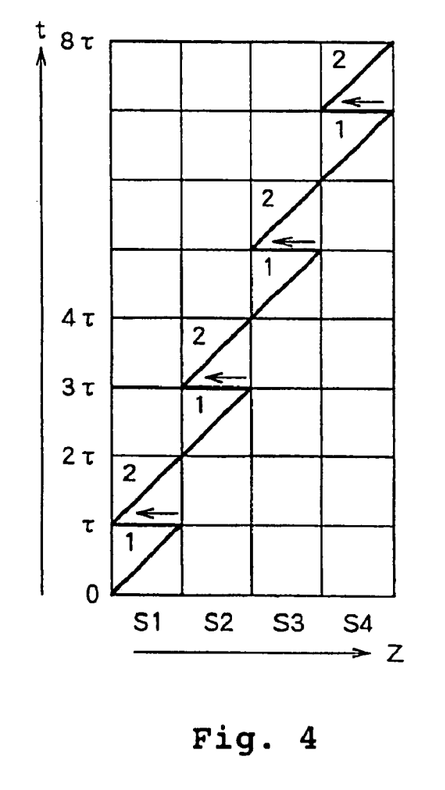
FIG. 4 is a diagram for explaining an address selection sequence according to one embodiment of the present invention.

Referring to FIGS. 3 and 4, a conventional address scanning method and the address scanning method of the present embodiment will be compared. FIG. 3 shows a conventional address scanning method and FIG. 4 shows the address scanning method of the present embodiment. In FIGS. 3 and 4, the horizontal axis represents the Z direction and the vertical axis represents an elapsed time t. Here, it is assumed that both the electronic scanning rate and the mechanical scanning rate are the same in the conventional method and the method of the present embodiment.

As shown in FIG. 3, in the conventional method, the beam addresses are not divided into groups, and the beam addresses are sequentially selected one by one from the first beam address to the n-th (last) beam address. Namely when attention is paid to one address scanning operation as a whole, each address is selected only once. Therefore, 4 τ is required for scanning all the beam addresses, and 8 τ is required for carrying out address scanning twice so as to obtain a differential image.

According to the present embodiment, on the other hand, as shown in FIG. 4, address scanning is carried out twice (two-times of sub-scanning) for each address group. Specifically, with regard to the address group S1, for example, the first address scanning operation is carried out, which takes time τ, and subsequently the second address scanning operation is carried out, which takes another time τ. Then, with regard to the address group S2, the first address scanning which takes time τ is carried out and this is followed by the second address scanning which takes another time τ. In this manner, address scanning is similarly carried out with regard to the address groups S3 and S4. As a result, 8 τ is required for carrying out address scanning for all the beam addresses.

Therefore, when the time required for one scanning operation in the Z direction from the start point to the end point is simply compared between the conventional method and the method of the present embodiment, the method of the present embodiment takes twice as much time as the conventional method. However, the total time required for forming a differential image is 8 τ for both the conventional method and the method of the present embodiment. According to the present embodiment, address scanning is carried out twice for each address group (namely, for each "partial space" in the three-dimensional echo data acquisition space). In this case, the time interval between the two address scanning operations is short. When attention is focused on a certain beam address, for example, according to the present embodiment, the time required from the first wave transmission/reception (formation of an ultrasonic beam) to the second wave transmission/reception (formation of an ultrasonic beam) can be a quarter that required for the conventional method. This makes it possible to achieve two beam scanning operations with a short interval between them for each partial space corresponding to each address group. As a result, it is possible to clearly image sharp changes caused in the partial space. This advantage can be achieved over the whole three-dimensional echo data acquisition space.

Therefore, when, for example, an ultrasonic contrast agent is injected into a living body and the behavior of the ultrasonic contrast agent within the living body is observed from the time point immediately after the injection, it is possible to perform a differential operation on two items of image data (which may be either pixel data or echo data) for each partial space. This results in formation of an ultrasonic image which accurately reflects the behavior of the ultrasonic contrast agent. It should be noted, however, the differential operation is not necessarily performed.

Figure 5:
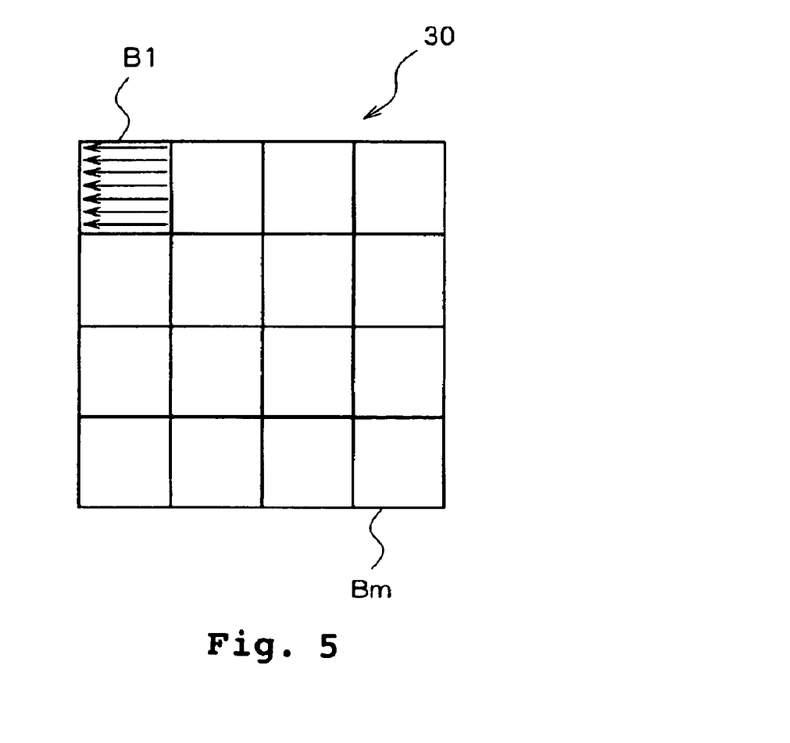
FIG. 5 is a diagram for explaining an address selection sequence according to another embodiment of the present invention.
Figure 6:
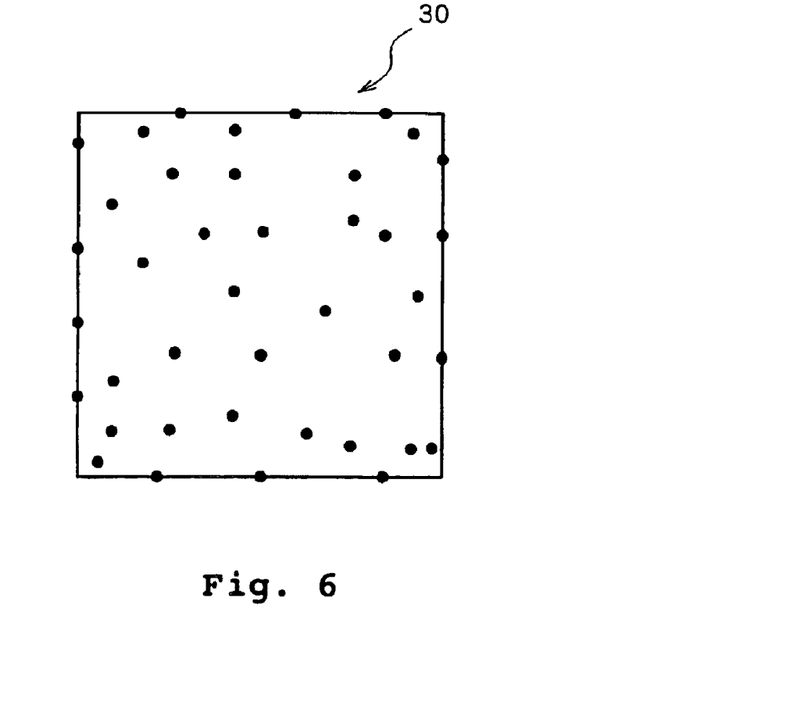
FIG. 6 is a diagram for explaining an address selection sequence according to still another embodiment of the present invention.

FIGS. 5 and 6 illustrate other example scanning methods. In the example shown in FIG. 5, the beam address array 30 is divided into a plurality of blocks B1~Bm which are arranged in a matrix. For each block, a plurality of ultrasonic beam scanning operations are carried out concurrently, and such beam scanning is repeated twice. This method also provides an operational effect similar to that in the method of FIG. 4. It should be noted that when the beam addresses selection method as shown in FIG. 5 is employed, it is preferable to use a two-dimensional array transducer so that electronic scanning in both X and Z directions can be achieved. This is similarly applied to the method shown in FIG. 6, which will be described below.

In the example arrangement shown in FIG. 6, one address group is composed of a plurality of addresses indicated by black circles which are randomly arranged, and a plurality of such address groups are included in the beam address array 30 as a whole. As in the examples described above, address scanning is carried out a plurality of times for each address group. This method can also provide the operational advantage which is similar to that in the above-described methods.

Figure 8:
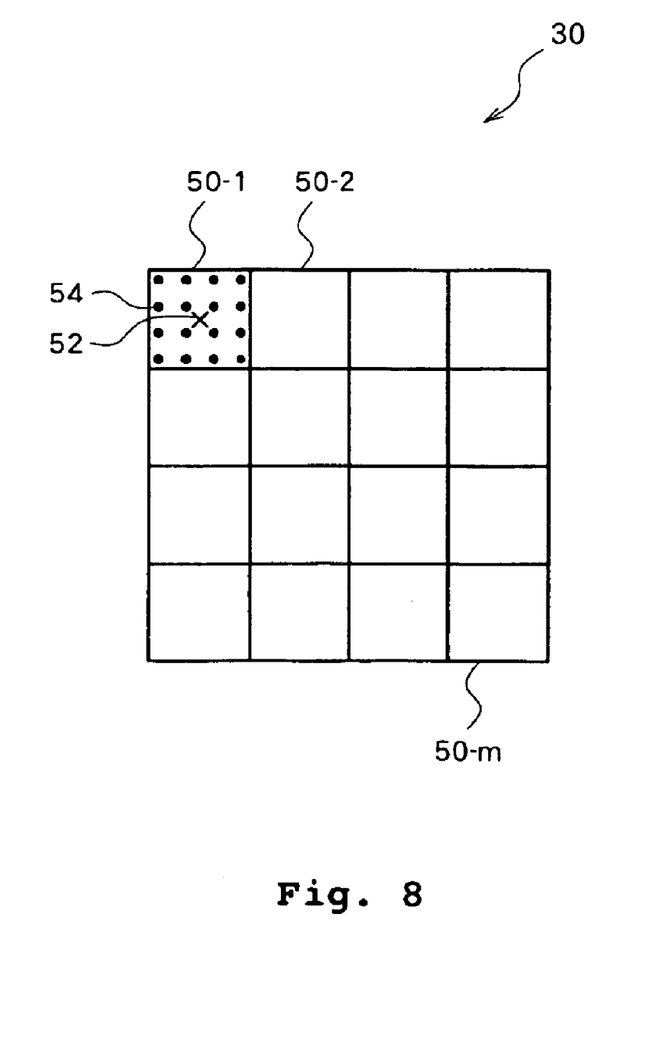
FIG. 8 is a diagram for explaining an address selection sequence used when a plurality of receiving beams are formed simultaneously for one transmitting beam.

FIG. 8 shows a still another example of a scanning method. A two-dimensional array transducer is used in this example. Many "receiving" beam addresses indicated by black dots which are arranged in a matrix are shown in the beam address array 30. A transmitting beam address 52 is indicated by a symbol X. The beam address array 30 is divided into m blocks 50, namely a block 50-1~a block 50-m. For each of the first to the m-th blocks, transmission and reception of ultrasonic waves is performed twice in sequence. Specifically, in the block 50-1, one broad transmitting beam is formed about the transmitting beam address X, and immediately after that, 16 receiving beams, for example, are concurrently formed. Subsequently, with regard to this block 50-1, the similar transmission and reception of ultrasonic waves is repeated. Next, with regard to the block 50-2, transmission and reception of ultrasonic waves is performed twice in a manner similar to that in the block 50-1. This operation is repeated until the ultrasonic wave transmission and reception is performed with regard to the last block 50-m. In summary, ultrasonic wave transmission and reception is carried out (2×m) times for the whole beam address array 30. This method also allows acquisition of two items of image data (echo data) for each block within a short time period.

Figure 7:
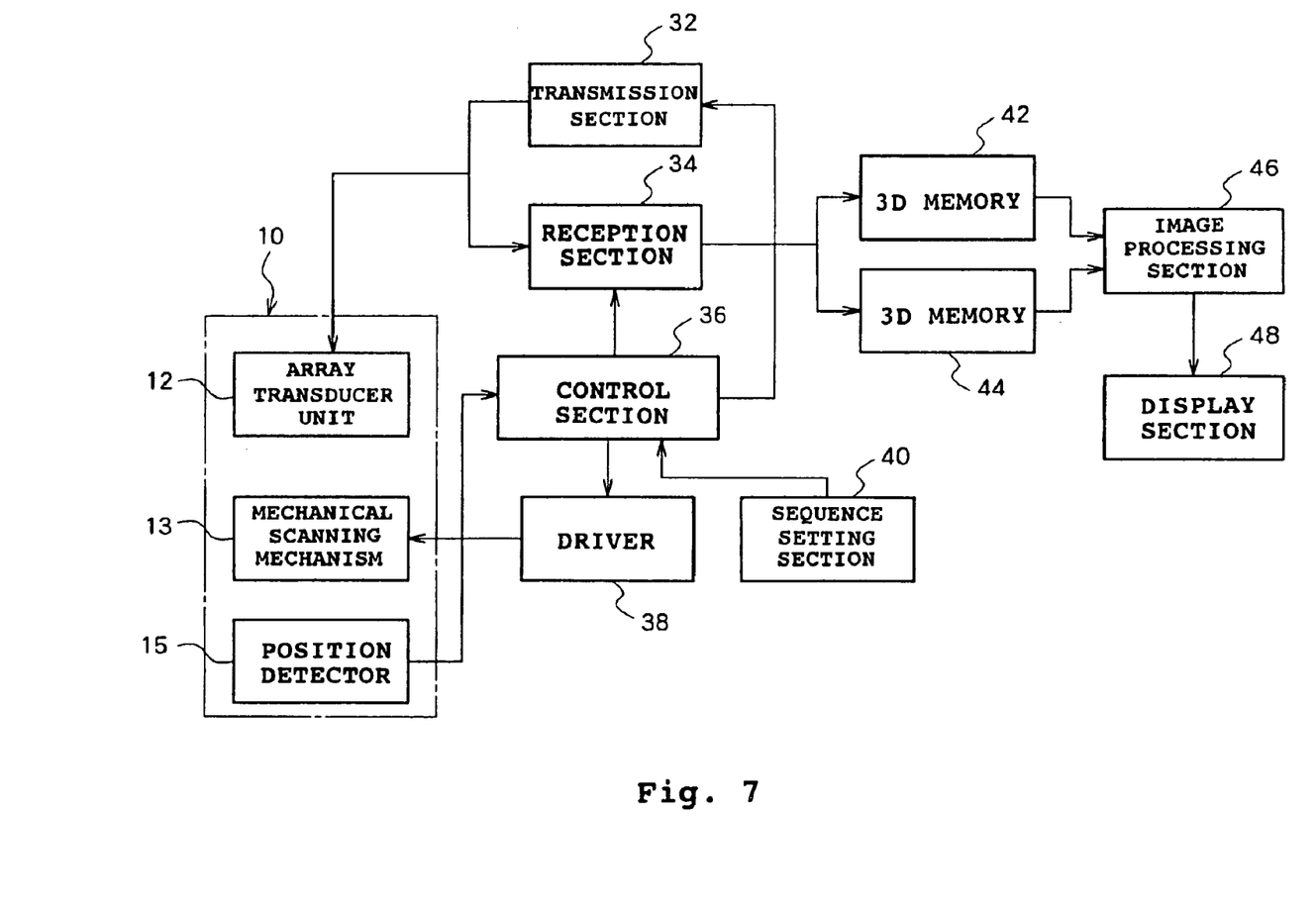
FIG. 7 is a block diagram showing a ultrasonic diagnostic apparatus according to an embodiment of the present invention.

FIG. 7 is a block diagram showing the overall structure of an ultrasonic diagnostic apparatus for implementing the scanning method shown in FIG. 4.

The three-dimensional echo data acquiring ultrasonic probe 10 includes an array transducer unit 12, a mechanical scanning mechanism 13, a position detector 15 or the like, as shown in FIG. 1.

The position detector 15 detects the position of the array transducer unit 12 in the mechanical scanning direction or the Z direction, and outputs a detection signal to a control section 36 which will be described later. A transmission section 32 is connected with the array transducer unit 12, and a plurality of transmitting signals are supplied from the transmission section 36 to a plurality of transducer elements.

A reception section 34 is also connected with the array transducer unit 12, and a plurality of receiving signals are supplied from the plurality of transducer elements to the reception section. In the reception section 34, a phase-shift and addition operation is performed with respect to the plurality of receiving signals. Namely, the transmission section 32 functions as a so-called transmitting beam former and the reception section 34 functions as a receiving beam former. When k receiving beams are formed per one transmitting beam, normally k reception sections are provided in parallel.

The control section 36 controls the electronic and mechanical scanning in accordance with the iterative sequence for address selection, which is used for achieving the iterative address scanning for each address group.

A sequence setting section 40 is formed as input means which is operated by a user. The sequence setting section 40 enables the user to set the address groups as desired and to set the number of iterative address scans for each address group as desired. Data regarding the iterative selection sequence thus set is stored in a memory provided in the control section 36. The control section 36 controls the mechanical scanning by means of the mechanical scanning mechanism 13 and the electronic scanning of the ultrasonic beams in accordance with the iterative sequence data read from the memory. When a control signal is input to a driver 38 from the control section 36, the driver 38 supplies a drive signal to the driving motor in the mechanical scanning mechanism 13 in accordance with the control signal.

In the example structure shown in FIG. 7, two three-dimensional (3D) memories 42, 44 are provided downstream of the reception section 34. The 3D memory 42 stores, for each address group, a plurality of receive signals (an echo data set) obtained by the first scanning. The 3D memory 44 stores, for each address group, a plurality of receive signals (an echo data set) obtained by the second scanning. As a matter of course, these memories can be formed as a single memory.

An image processing section 46 has a function to calculate, for each address group, a difference between the echo data (or image data) obtained by the first address scanning and the echo data (or image data) obtained by the second address scanning, thereby forming a three-dimensional differential image. In this manner, a partial differential image (a partial image) is formed for each address group (namely, for each partial space). The image processing section 46 combines a plurality of partial images to thereby form a three-dimensional differential image which represents a whole three-dimensional echo data acquisition space. The three-dimensional differential image thus formed is displayed on the display section 48. The processing method used by the image processing section is not limited to the differential operation described above. For example, it is possible to combine the echo data obtained by the fist beam scanning and the echo data obtained by the second beam scanning using a predetermined operation. Methods of forming a three-dimensional image include various methods such as integration, maximum detection, average detection, volume rendering, and so on.

As described above, the three-dimensional differential image enables the behavior or change of an ultrasonic contrast agent, for example, to be clearly visualized. This leads to an advantage that information important for diagnosis of a disease can be provided.

In the present embodiment, it is also possible to make an address group correspond to one scanning plane. Further, while the array transducer unit 12 is moved for mechanical scanning in the embodiment shown in FIG. 7, it is also possible to use a two-dimensional array transducer so that address scanning in accordance with the iterative sequence which is similar to that described above can be achieved under the electronic control of the transducer, as described above. This method is more convenient because the necessity of actually moving the array transducer can be eliminated.

As described above, according this embodiment, it is possible to provide a new address scanning method for forming a three-dimensional echo data acquisition space. This address scanning method is especially suitable for forming an image of an ultrasonic contrast agent.

What is claimed is:

1. An ultrasonic diagnostic apparatus comprising:
    group setting means for setting a plurality of address groups with regard to a beam address array which corresponds to a three-dimensional echo data acquisition space, each address group corresponding to each partial space within the three-dimensional echo data acquisition space;
    sequence setting means for setting an iterative sequence of beam addresses, which is used for selecting a plurality of beam addresses constituting said beam address array wile selecting beam addresses repeatedly for each of said address groups;
    address selecting means for selecting the beam addresses in accordance with the iterative sequence which is set by said sequence setting means;
    beam forming means for forming an ultrasonic beam at a beam address selected by means of said address selecting means to thereby repeatedly form a set of ultrasonic beams for every partial space; and
    image forming means for forming an ultrasonic image which represents existence or behavior of an ultrasonic contrast agent within the three-dimensional echo data acquisition space based on echo data acquired by repeatedly forming a set of ultrasonic beams for every partial space.

2. An ultrasonic diagnostic apparatus according to claim 1, wherein
    each of said partial spaces is composed of one or more scanning planes, and
    each of said scanning planes is composed of a plurality of ultrasonic beams which are sequentially formed in the electronic scanning direction.

3. An ultrasonic diagnostic apparatus according to claim 1, wherein
    said image forming means uses two items of echo data obtained at the same beam address at a predetermined time interval, to form an ultrasonic image representing a change within said predetermine time interval.

4. An ultrasonic diagnostic apparatus according to claim 3, wherein
    said image forming means includes a differential operation unit for executing a differential operation with regard to said two items of echo data.

5. An ultrasonic diagnostic apparatus according to claim 1, wherein
    said beam forming means includes:
    a transducer unit having a one-dimensional array transducer for electronically scanning said ultrasonic beams; and
    a mechanical scanning mechanism for moving said transducer unit for mechanical scanning.

6. An ultrasonic diagnostic apparatus according to claim 5, wherein
said mechanical scanning mechanism moves said transducer unit for mechanical scanning in accordance with said iterative sequence.

7. An ultrasonic diagnostic apparatus according to claim 6, wherein
in the process of moving said transducer unit forward in the mechanical scanning direction, said mechanical scanning mechanism causes said transducer unit to move backward in steps.

8. An ultrasonic diagnostic apparatus according to claim 1, wherein
said beam forming means includes a two-dimensional array transducer, and
said ultrasonic beams are electronically scanned two-dimensionally.

9. An ultrasonic diagnostic apparatus according to claim 1, wherein
said beam forming means performs scanning of said ultrasonic beams in the first scanning direction to form a scanning plane, and moves the position of said scanning plane forward in the second scanning direction, and
in the process of moving the position of said scanning plane forward in the second scanning direction, such forward movement is repeated for each section corresponding to each of said address groups.

10. An ultrasonic diagnostic apparatus according to claim 1, wherein
said plurality of address groups are provided in a matrix with regard to said beam address array.

11. An ultrasonic diagnostic apparatus according to claim 10, wherein
each of said address groups is composed of a plurality of beam address lines, and
ultrasonic beams are electronically scanned for each of said beam address lines.

12. An ultrasonic diagnostic apparatus according to claim 1, wherein
each of said address groups is composed of a plurality of beam addresses randomly provided in said beam address array.

13. An ultrasonic diagnostic apparatus according to claim 1, wherein
said beam address array is composed of a plurality of receiving beam addresses, and
at each of said address groups, for one transmission and reception of said ultrasonic beam, one transmitting beam is formed and a plurality of receiving beams are concurrently formed.

14. An ultrasonic diagnostic apparatus comprising:
a setting section for setting a plurality of address groups with regard to a two-dimensional beam address array which corresponds to a three-dimensional echo data acquisition space, each address group corresponding to each partial space within the three-dimensional echo data acquisition space;
a sequencer for setting a sequence used for selecting a plurality of beam addresses constituting said beam address array while selecting beam addresses repeatedly for each of said address groups;
an address controller for selecting beam addresses in accordance with the sequence set by said sequencer;
a beam former for forming an ultrasonic beam at a beam address selected by said address controller to thereby repeatedly form a set of ultrasonic beams for every partial space; and
an image forming section for forming an ultrasonic image which represents existence or behavior of an ultrasonic contrast agent within the three-dimensional echo data acquisition space based on echo data obtained by repeatedly forming a set of ultrasonic beams for every partial space.

15. An ultrasonic diagnostic apparatus according to claim 14, wherein
for each of said address groups, a step of sequentially selecting a plurality of beam addresses of the address group is repeated at least twice.

16. An ultrasonic diagnostic apparatus according to claim 14, wherein
said beam address array is composed of a plurality of receiving beam addresses, and
for each of said address groups, a step of collectively selecting a plurality of receiving beam addresses of the address group is repeated at least twice.

17. An ultrasonic diagnostic apparatus for forming a three-dimensional echo data acquisition space within tissue of a living body in which an ultrasonic contrast agent is injected, said apparatus comprising:
means for setting a plurality of partial spaces in said three-dimensional echo data acquisition space;
means for effecting beam scanning with regard to said three dimensional echo data acquisition space by repeating transmission and reception of an ultrasonic wave plurality of times for each of said partial spaces;
means for forming a partial image representing the existence or behavior of said ultrasonic contrast agent based on echo data obtained by transmitting and receiving an ultrasonic wave a plurality of times for each of said partial spaces; and
means for synthesizing partial images regarding said plurality of partial spaces to form an ultrasonic image.

18. A two-dimensional ultrasonic beam scanning method for forming a three-dimensional echo data acquisition space within tissue of a living body in which an ultrasonic contrast agent is injected, said method comprising the steps of:
determining a plurality of partial spaces with regard to said three dimensional echo data acquisition space;
setting a sequence used for sequentially selecting said plurality of partial spaces while selecting each of said plurality of partial spaces a plurality of times; and
two-dimensionally scanning an ultrasonic beam in accordance with said sequence, in which a set of ultrasonic beams is repeatedly formed in each partial space.

* * * * *